United States Patent [19]

Corbet et al.

[11] Patent Number: 4,576,477
[45] Date of Patent: Mar. 18, 1986

[54] METHOD AND APPARATUS FOR MEASURING DENSITY PROFILES IN MICROSCOPIC TUBE FLOW

[75] Inventors: Aaron B. Corbet, Palo Alto, Calif.; Christoph Holliger, Boniswil, Switzerland; Bruno Strul, Palo Alto, Calif.

[73] Assignee: The United States of America as represented by the Department of Health and Human Services, Washington, D.C.

[21] Appl. No.: 390,876

[22] Filed: Jun. 22, 1982

[51] Int. Cl.$^4$ .................. G01N 33/48; G01N 21/05
[52] U.S. Cl. .................................. 356/39; 250/576; 356/442
[58] Field of Search ............... 356/39, 40, 318, 335, 356/244, 246, 442; 250/576

[56] References Cited

U.S. PATENT DOCUMENTS

| | | | |
|---|---|---|---|
| 2,875,666 | 3/1959 | Parker et al. | 356/39 |
| 3,275,834 | 9/1966 | Stevens | 356/39 X |
| 3,390,229 | 6/1968 | Williams | 356/39 X |
| 3,413,464 | 11/1968 | Kamentsky | 356/39 X |
| 3,699,336 | 10/1972 | Ehrlich et al. | 356/39 X |
| 3,790,760 | 2/1974 | Stiller | 356/335 X |
| 3,873,204 | 3/1975 | Friedman et al. | 356/39 |
| 3,941,479 | 3/1976 | Whitehead | 356/39 X |
| 3,976,862 | 8/1976 | Curbelo | 356/39 X |
| 4,028,553 | 6/1977 | Farcinade | 250/576 |
| 4,058,737 | 11/1977 | Takahashi et al. | 250/573 |
| 4,095,904 | 6/1978 | Klein et al. | 250/576 X |
| 4,265,538 | 5/1981 | Wertheimer | 250/576 X |

FOREIGN PATENT DOCUMENTS 2201524  7/1973  Fed. Rep. of Germany ........ 356/39

OTHER PUBLICATIONS

Francini et al, "Electro-Optical Granulometer for Measurements of Flowing Particles", Optics and Laser Technology, vol. 14, #2, Apr. 1982, pp. 81-85.

Primary Examiner—Vincent P. McGraw
Attorney, Agent, or Firm—Holman & Stern

[57] ABSTRACT

Particle distribution in a fluid flowing through a microscopic tube is achieved by flowing the fluid vertically-downward through a transparent capillary tube and passing light through the flowing fluid. A linear array of photodiodes responds to light passing through the fluid by registering a series of signals representing the linear projection of particles passing through the plane defined by the light source and the photodiode array. The fluid is supplied from a reservoir which can be selectively pressurized by a gas to control the egress flow rate of fluid. A syringe serves as the egress path from the reservoir and a rotatable stirring rod is disposed in the syringe to stir the egressing fluid. The syringe feeds a disposable assembly which includes a hypodermic needle feeding the capillary tube which is mounted between a microscope slide and cover in the path of the sensing light.

23 Claims, 4 Drawing Figures

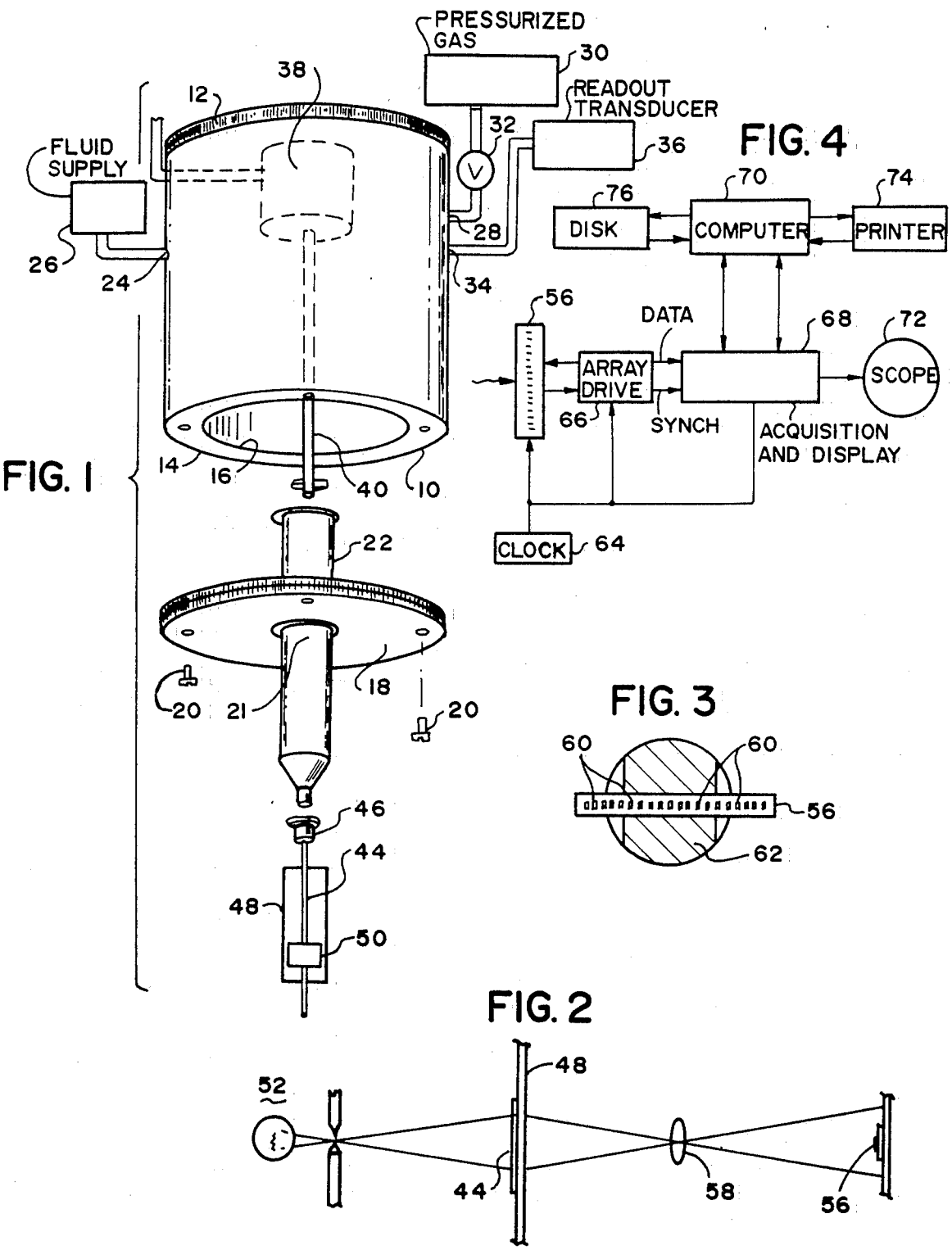

METHOD AND APPARATUS FOR MEASURING DENSITY PROFILES IN MICROSCOPIC TUBE FLOW

TECHNICAL FIELD

The present invention relates to measuring particle distribution in fluids flowing through microscopic flow channels. In a specific embodiment, the present invention relates to measuring particle distribution in flowing whole blood. Although the present invention is described primarily in terms of measuring particle distribution in whole blood, it should be understood that the techniques described herein relate to other types of fluids, particularly optically-dense fluids where the attenuation of light passing through larger volumes of the fluid, renders normal light transmission studies impossible.

BACKGROUND OF THE INVENTION

The circulatory system is the transport path through which nutrients and oxygen are carried to the tissues, carbon dioxide is returned to the lungs and metabolic products are distributed throughout the body. Blood, the carrier of these substances, is comprised of red blood cells, white blood cells, and platelets suspended in plasma. The study of blood rheology enables researches to evaluate the influences of regions of stasis, particle entrainment, red blood cell aggregation, shear rate, drag, etc., on blood flow. An understanding of these factors would provide significant insight into vascular functioning.

There has been considerable prior art interest shown in model tube experiments with flowing suspensions in order to gain a possible insight into vascular functioning. The results have been informative as regards random migration under collision, wall effects, the effect of particle concentration on velocity profiles, etc. Such experiments have generally been performed with abiological materials. For example, one prior art approach employs apparatus for determining the passage of a particle through any selected point on a tube cross-section by measuring the coincidence when a particle blocks two (2) mutually perpendicular light beams. In this approach, the internal diameter of the tube was approximately 11 mm and latex spheres were employed. The distribution of the particles was obtained by counting the particles as represented by the blocking of the two light beams. The disadvantages of this approach involves the macroscopic dimensions, the use of artificial latex spheres instead of actual blood particles, and the need for large sensors to count the particles.

In order to obtain information that is more definitive and applicable to the in vivo flow situation, it is desirable to work with actual blood samples in a state as close to physiological as possible. However, light transmission through normal hematocrit blood, flowing through macroscopic tubes, is so attenuated as to preclude informative measurements.

Light transmission through microscopic volumes of blood has long been the basis of our understanding of microvasculature. Recent advances in manufacturing technology have made capillary tubes of uniform microscopic bore commercially available. While this has extended the range of controlled in vitro experimentation, data acquisition has thus far been limited to net optical density measurements and high speed motion picture filming of particle behavior. Data processing, particularly in the latter case, is extremely laborious and time consuming.

SUMMARY OF THE INVENTION

It is therefore an object of the present invention to provide a method and apparatus for sensing particle distribution in optically-dense fluids such as blood which provides data in a small fraction of time suitable for high speed data processing.

It is another object of the present invention to provide an improved method and apparatus for measuring particle distribution in microscopic volume of flowing whole blood.

In accordance with the present invention, blood or similar fluid is caused to flow through a capillary tube in a vertically-downward direction through the path of a light beam. A linear photodiode array records a transverse projection of particle distribution across the capillary tube as the blood flows through the light beam. The photodiode array has high spatial resolution and sensitivity and provides data which is easily and quickly processed to provide a time average density distribution based on the light intensity distribution. Particle distribution data is accurately provided in a small fraction of the time previously required. The system allows for the use of small homogeneous volumes of blood, the simple addition of moieties to the samples, simple change of the capillaries and precisely controlled flow conditions.

Blood flow is provided from a reservoir which can be selectively pressurized by gas to control the output flow rate. A syringe projects from within the reservoir to supply an output passage and a stirrer is disposed in the reservoir and syringe so as to stir the fluid egressing from the reservoir. A disposable assembly including a hypodermic needle and the capillary tube can be connected to the syringe to permit the necessary flow through the capillary tube. The capillary tube is placed on a microscope slide between the glass slide and cover plate in the path of the sensing light. A small amount of immersion oil, of appropriate refractive index, is placed between the slide and the cover plate to eliminate optical distortion due to the refraction between the glass and air interface. Particle distribution data obtained with the described apparatus yields vital information on hydrodynamic and rheological forces for varying flow situations.

BRIEF DESCRIPTION OF THE DRAWINGS

The above and still further objects, features, and advantages of the present invention will become apparent upon consideration of the following detailed description of a specific embodiment thereof, especially when taken in conjunction with the accompanying drawings, wherein:

FIG. 1 is a partially schematic exploded view of the fluid flow portion of the system of the present invention;

FIG. 2 is a schematic diagram of the light imaging portion of the system of the present invention;

FIG. 3 is a detailed view of the photodiode array employed in the imaging arrangement of FIG. 2; and FIG. 4 is a functional block diagram of the data acquisition portion of the system employed in the present invention.

DESCRIPTION OF THE PREFERRED EMBODIMENTS

Referring specifically to FIG. 1 of the accompanying drawings, the flow portion of the system of the present invention includes a reservoir 10 having a generally hollow cylindrical form which is closed at one end by a circular end wall 12. The opposite end wall 14 is annular in configuration with a central opening 16 disposed coaxially with respect to the cylindrical reservoir. A cover plate 18 is disposed over end wall 14 to cover opening 16. Cover plate 18 is secured to end wall 14 by means of screws 20 or the like and has a generally annular configuration with a central hole 21 disposed coaxially with respect to the central longitudinal axis of reservoir 10. A syringe 22, without its plunger, is secured in the central hole 21 of cover plate 18 in a fluid sealing engagement such that the wider inlet end of the syringe is disposed within the reservoir 10 and the narrower outlet end of the syringe extends out from the reservoir past cover plate 18. A fluid inlet port 24 is provided at an appropriate location in reservoir 10 to receive test fluid for analysis from a fluid supply 26. A gas inlet port 28 receives pressurized gas from a pressurized gas supply 30 under the control of an adjustable valve 32. The gas selectively pressurizes the interior of reservoir 10 to force the test fluid through the syringe at the desired flow rate. A pressure transducer port 34 provides communication for connection to a read-out transducer 36 which permits an operator to monitor the pressure inside reservoir 10.

A small motor 38 is mounted on the interior surface of end wall 12 and rotatably drives a stirring rod 40 so that the rod rotates about its own longitudinal axis. The stirring rod 40 is preferably made of glass and extends coaxially within reservoir 10 and out through opening 16 in end wall 14. In this position, the stirring rod extends to the syringe 22. Motor 38 has terminals 42 extending outside the reservoir to permit application of a control voltage for the motor. Typically, motor 38 operates at approximately 5 rpm and rotates the stirring rod accordingly.

The reservoir 10, motor 38, stirring rod 40, and syringe 22 are preferably re-usable components; that is, these components can be re-used for different measurements and different fluids. A disposable portion of the flow system includes a transparent capillary tube 44, preferably made of glass, which is secured by epoxy, or the like, to the inlet end of a disposable hypodermic needle 46. The hypodermic needle 46 is of the blunt end type and can be connected to the outlet end of the syringe 22 in a fluid conducting connection. The outlet end of the hypodermic needle 46 and the capillary tube 44 are affixed to a transparent microscope slide 48. The portion of the capillary tube to be monitored is placed between the slide 48 and a transparent cover plate 50. A drop of immersion oil, of appropriate refractive index, is placed between the slide end 48 and cover plate 50 to eliminate optical distortion due to the refraction between the glass-air interface. The only refractive distortion remaining therefore, is that due to the test fluid-glass interface in the capillary tube. Provisions for mathematical compensation of this distortion can be effected by well known techniques.

Test fluid injected into the reservoir via port 24 is caused to flow out of the reservoir, via syringe 22, by the application of pressurized gas to the reservoir at port 28. By controlling the applied gas pressure, the rate of outflow from the reservoir can be controlled. Stirring rod 40 slowly stirs the egressing fluid in syringe 22 to minimize stasis and ensure a continuing flow. The entire assembly is arranged with the capillary tube 44 extending vertically downward so that the flow therethrough is in a vertically-downward direction. As described below, the portion of the capillary tube 44 which resides between the cover plate 50 and slide 48 is disposed in the field of an ordinary light transmission microscope which is affixed to a sturdy support, such as a heavy bench, such that its light beam is directed horizontally and perpendicular to the direction of flow. This vertical downflow through the capillary tube eliminates any gravitational anisotrophy in the flow and also permits simpler data processing.

Referring now to FIGS. 2 and 3 of the accompanying drawings, the light imaging system of the present invention, is illustrated as including an ordinary light transmission microscope which is, as noted above, affixed to a heavy structural support. A light source 52 emits a light beam which travels along a path, generally indicated by the reference numeral 54, which passes perpendicularly through the capillary tube 44. The real image of the capillary flow is cast upon a photodiode array 56 by means of a projection lens 58 disposed between the capillary tube and array 56. The photodiodes 60 in array 56 are successively spaced by equal distances along a horizontal path which faces the light source 52. As best illustrated in FIG. 3, the image 62 of the capillary tubing which is cast onto the photodiode array 56 is somewhat less in width than the horizontal length of the photodiode array. This can be achieved by appropriate positioning of the elements of the microscope and the magnification effected therein.

The median plane through the capillary tube 44 is found by coarse focussing the microscope until the capillary tube image 62 is of maximum width. The microscope is then fine-focussed until the dark refraction fringe of the capillary tube-liquid interface barely falls inside the bright fringe.

Light source 52 may be any suitable light source to serve the intended purpose. For example, a xenon arc lamp has been employed to obtain data samples described below. However, a strobe light, having pulse widths on the order of 5 microseconds, can also be used. The strobe light can be synchronized to the sample and hold circuit described below in relation to FIG. 4 to allow more nearly instantaneous density profile "snapshots" in the case of faster flow through the capillary tube. When a xenon arc lamp source is employed, the upper limit on the monitorable flow rate is on the order of 1 cm/sec, in order to keep the data processing relatively simple. This flow rate is consistent with physiological flow, in terms of the size of capillary tubing employed. When strobe light sources are employed, the upper limit of monitorable flow can be increased by a factor of 100.

The photodiode array may be any standard commercial unit, such as the unit manufactured by EG & G Reticon, G-Series. For example, the elements may be equally spaced with a density of 256 photodiodes per ¼ inch, or 1,024 diodes per inch. Other densities and configurations are possible; this particular example allows for a very high spatial resolution along a single dimensional line across the capillary tube.

Referring to FIG. 4 of the accompanying drawings, a typical data acquisition section of the system is illustrated in block diagram form. Specifically, light which is incident on the photodiode array 56 is converted to an electric charge which is integrated and stored in the diode capacitance which is inherent in the array assembly. This charge is sequentially read-out from each diode at a rate determined by clock 64. Clock 64 provides synchronization signals to an array drive circuit 66, an acquisition and display circuit 68 and to the array of photodiodes 56. The clock rate may be adjustable in a conventional manner and determines the integration time of the photodiodes. The output signal from each diode is sampled and held sequentially at the array drive circuit 66 to form a continuous video signal of time-integrated distribution across the array. This video signal is digitized and stored at the acquisition and display circuit under the control of a mini-computer 70 utilizing fast analog-to-digital conversion techniques. The mini-computer may be, for example, a PDP 11-10 mini-computer. Alternatively, the mini-computer may be a DEC RT-11 model.

Processed signals may be displayed on a cathode ray tube oscilloscope 72. Numerical data may also be printed out on a line printer 74 and records may be stored on disc 76.

The present invention is primarily concerned with the combination of the flow portion of the system, illustrated in FIG. 4, and the light imaging portion of the system, illustrated in FIG. 2. The data acquisition and display portion of the system illustrated in FIG. 4 is described herein for general interest only and to show the general nature of the components which would be employed to acquire and display the data which is made available by the present invention. In order to facilitate an understanding of how the data acquisition and display circuit may be employed, a detailed description of the rationale behind the acquisition and display is described in the following paragraph.

Under appropriate circumstances, the presence or absence of an opaque particle at some position in the capillary tubing 44 is quite well approximated by an off or on signal, respectively, at the photodiode array 56. This assumes that the incident light intensity is high enough so that variations due to Beer's Law are relatively small by comparison. In this approximation, the normalized particle distribution, as seen by light traversing the capillary tube at the fractional coordinate $\alpha$, is:

$$\rho(\alpha) = \frac{1}{N} \Sigma \sigma_n(\alpha) = 1 - \frac{1}{N} \cdot \Sigma \frac{I_n(\alpha)}{\overline{I}} \qquad (1)$$

wherein the sum is over N profile snapshots, and $\sigma_n = 1, 0$, for the presence or absence, respectively, of a particle at the fractional coordinate $\alpha$ in the $i^{th}$ profile. It is assumed that the suspension is dilute enough so that the possibility of more than one particle occurring simultaneously at the projected coordinate $\alpha$ is an extremely rare event. Nevertheless, on the assumption that particles with the same fractional X-coordinates, $\alpha = x/R$, are equally opaque, a projected particle distribution would be provided. In a truly continuum description, the radial distribution being sought is related to the projected distribution by an integral transformation which can be extremely difficult to invert analytically. In practice, one generally deals with some discrete representation of the distance intervals. Thus, in the present example, $\alpha$ can be decomposed into from 50 to 256 discrete intervals. This converts the integral transform of Equation (1) to a linear transformation of the form:

$$\vec{\rho}(\alpha) = \hat{A}\vec{\rho}(\epsilon); \epsilon \equiv r/R \qquad (2)$$

which is readily inverted to provide the desired radial distribution. The detailed derivation for this form of linear transformation, as well as its application to data analysis for the case of a relatively coarse decomposition, may be found in "The Intra-Luminal Distribution Of 15 Micron Diameter Carbonized Microspheres Within Arterial Microvessels As Determined By Vital Microscopy Of The Golden Hamster Cheek Pouch", by Harell, et al., appearing in Microvascular Research, Volume 18, pages 384–402, 1979. In the present invention, the condition of true radial symmetry, and a fine decomposition of the distance interval, renders this method much more accurate. However, owing to the relatively shallow depth of field employed here, the image of particles outside of the focal plane will be obscured by scattered light to an extent that increases with distance from the median plane. As an approximation, this can be written, then, as:

$$\rho(\alpha,\beta) \propto e^{-\lambda|\beta|} \qquad (3)$$

wherein $\lambda$ is an empirically determined fall-off distance. Combining the Equation (3) and Equation (2), we than have:

$$\vec{\rho}(x) = \Sigma A_{ij}\rho_j(\alpha,\beta)e^{-\lambda|\beta|} \text{ or,} \qquad (4)$$

$$\vec{\rho}(x) = \underline{\hat{A}}\vec{\rho}(r) \qquad (5)$$

wherein $\hat{A}$ is the new matrix defined via Equation (4). Again, this is a non-singular matrix which is readily inverted.

The parameter $\lambda$ can be evaluated in several ways. For example, one may affix an opaque particle to the interior capillary wall, fill the capillary tube with test fluid, rotate the capillary tube and then tabulate the transmitted light intensity at the particles' respective $\alpha$-coordinates versus the rotation angle. A plot of the natural logarithm of intensity versus the cosine of the rotation angle should then yield an approximately straight line with the slope $-\lambda$.

At low light levels, imperfections in lenses and optical alignments lead to strong inhomogeneities and ansiotropies in light profiles. Furthermore, for light levels from low to moderate, it is necessary to subtract the photodiode array dark current (which is called "baseline" in the program of Appendex A) from the sample profiles in order to obtain accurate and symmetrical profiles.

At high light levels, the intrinsic dark response is "bleached out" of the array read-out so that uncorrected computer samples are themselves most accurate.

Appendix A is a program listing for the data acquisition and averaging of light intensity profiles.

The invention as described herein is an apparatus and method for making available data at the photodiode array which can be readily processed and analyzed to yield accurate density profile information in the microscopic tube flow from the capillary tube 44. The vertically-downward flow through the capillary tube and the perpendicularly oriented light passing through the capillary tube to the photodiode represent the essence of the invention and the means whereby the data can be provided for simple processing and analysis.

While we have described and illustrated a specific embodiment of our invention, it will be clear that variations of the details of constructions which are specifically illustrated and described may be resorted to without departing from the true spirit and scope of the invention as defined in the appended claims.

What is claimed is:

1. Apparatus for use in determining the density profile of a flowing concentrated suspension test fluid, said apparatus comprising:
    a transparent capillary tube;
    means for flowing said concentrated suspsension test fluid vertically downward through said capillary tube;
    light microscope means for transmitting light through said capillary tube and said flowing concentrated suspension test fluid in a horizontal direction perpendicular to the flow direction of said concentrated suspension test fluid, said microscope means comprising an array of photodiodes and means for focusing on said array an image of the concentrated suspension test fluid flowing through said capillary tube and said transmitted light;
    wherein said array of photodiodes is a horizontal linear array which extends to a greater length than the horizontal dimension of said test fluid image focused on said array; and
    data acquisition and display means responsive to said photodiodes for displaying density profile information for said concentrated suspension test fluid.

2. The apparatus according to claim 1, wherein said capillary tube is made of glass.

3. The apparatus according to claims 1 or 2, wherein said means for flowing comprises:
    a reservoir for said test fluid;
    a hypodermic needle for delivering said test fluid to said capillary tube; and
    syringe means for delivering said test fluid from said reservoir to said hypodermic needle.

4. The apparatus according to claim 3, wherein said syringe means includes an elongated syringe extending through a wall of said reservoir, and wherein said means for flowing further comprises:
    an elongated glass stirring rod having a longitudinal axis and disposed in said reservoir and extending longitudinally into said syringe; and
    motor means for rotating said stirring rod about said longitudinal axis.

5. The apparatus according to claim 4, wherein said means for flowing further includes:
    a test fluid supply port defined in said reservoir for delivering said test fluid into said reservoir; and
    a gas supply port defined in said reservoir for delivering pressurized gas into said reservoir to control the flow rate of test fluid through said syringe.

6. The apparatus according to claim 5, wherein said capillary tube and said hypodermic needle are secured together by epoxy in a disposable unit.

7. The apparatus according to claim 5, further comprising:
    a transparent planar microscope slide;
    a transparent slide cover; and
    means securing said capillary tube to said glass slide between said slide and said cover.

8. The apparatus according to claim 7, further comprising immersion oil disposed between said slide and said cover to surround the capillary tube portion between the slide and cover, wherein the light passing through said capillary tube and flowing fluid passes through said slide and said cover.

9. The apparatus according to claim 1, wherein said means for flowing includes:
    a reservoir for said test fluid;
    a test fluid supply port defined in said reservoir; and
    a gas supply port for delivering pressurized gas into said reservoir to control the flow rate of test fluid from said reservoir.

10. The apparatus according to claim 1, further comprising:
    a transparent planar microscope slide;
    a transparent slide cover; and
    means securing said capillary tube to said glass slide between said slide and said cover.

11. The apparatus according to claim 10, further comprising immersion oil disposed between said slide and said cover to surround the capillary tube portion between the slide and cover, wherein the light passing through said capillary tube and flowing fluid passes through said slide and said cover.

12. The apparatus according to claims 1 or 11, wherein said microscope means includes a xenon arc light source.

13. The apparatus according to claims 1 or 12, wherein said microscope means includes a periodic strobe light source.

14. The apparatus according to claim 1, wherein said means for focussing comprises a projection lens disposed between said capillary tube and said array of photodiodes.

15. The apparatus according to claim 1, wherein said photodiodes are successively spaced by equal distances with the density on the order of 1024 diodes to the inch.

16. The apparatus according to claim 1, further comprising:
    clock means for providing a periodic time synchronizing signal; and
    signal sample and hold means responsive to said time synchronizing signal for sequentially delivering sampling and integrating signals from said photodiodes.

17. The apparatus according to claim 1, wherein said test fluid is whole blood.

18. A method for use in determining the density profile of a flowing concentrated suspension test fluid, said method comprising the steps of:
    flowing the concentrated suspension test fluid vertically-downward through a transparent capillary tube;
    passing light through the capillary tube and the flowing concentrated suspension test fluid in a direction perpendicular to the concentrated suspension test fluid flow through said capillary tube;
    imaging the concentrated suspension test fluid which flows through the capillary tube and through the passing light onto a horizontally extending linear array of photodiodes having a greater horizontal array length than the horizontal dimension of the image of the concentrated suspension test fluid at said array; and
    acquiring and displaying density profile information for said concentrated suspension test fluid from said array of photodiodes.

19. The method according to claim 18, wherein the step of flowing the test fluid includes the steps of:

forcing the test fluid out from a reservoir by delivering gas under pressure to the reservoir; and stirring the test fluid in the reservoir before it is forced therefrom.

20. The method according to claims 18 or 19, wherein the step of passing light includes periodically pulsing a light source to provide a periodically interrupted beam of light which is passed through said capillary tube.

21. The method according to claim 18, further comprising the step of sequentially sampling and integrating signals provided by said photodiodes.

22. The method according to claim 18, wherein said test fluid is whole blood.

23. The method according to claim 18 wherein the step of passing light includes the steps of:
 emitting a series of light pulses having pulse widths on the order of a few microseconds toward said capillary tube; and
 focusing the light pulses passing through said capillary tube onto said array of photodiodes.

* * * * *